United States Patent [19]

Walker

[11] Patent Number: 4,991,743

[45] Date of Patent: Feb. 12, 1991

[54] CONTROLLED FLOW ACCUMULATOR

[75] Inventor: John C. Walker, Louisville, Colo.

[73] Assignee: Cobe Laboratories, Inc., Lakewood, Colo.

[21] Appl. No.: 432,364

[22] Filed: Nov. 6, 1989

[51] Int. Cl.⁵ .............................................. B65D 35/28
[52] U.S. Cl. ................................. 222/103; 222/386.5; 604/132
[58] Field of Search ...................... 222/103, 92, 95, 96, 222/390, 386.5; 604/132, 154, 155

[56] References Cited

U.S. PATENT DOCUMENTS

| 103,640 | 5/1870 | Merritt | 222/103 |
|---|---|---|---|
| 2,761,445 | 9/1956 | Cherkin | 604/154 |
| 3,565,292 | 2/1971 | Jinotti | 222/103 |
| 3,625,401 | 12/1971 | Terry | 222/103 |
| 3,902,635 | 9/1975 | Jinotti | 222/103 |
| 4,157,771 | 6/1979 | Smith | 222/103 |

FOREIGN PATENT DOCUMENTS

| 2723131 | 11/1978 | Fed. Rep. of Germany | 222/103 |
|---|---|---|---|
| 330783 | 6/1930 | United Kingdom | 222/390 |

Primary Examiner—Andres Kashnikow
Assistant Examiner—Kenneth Bomberg

[57] ABSTRACT

A fluid flow control apparatus including a fluid flow portion configured to receive a flexible fluid container and an actuating portion which provides a variable force to the fluid flow portion thereby causing the fluid flow portion to pressurize the flexible fluid filled container.

6 Claims, 2 Drawing Sheets

CONTROLLED FLOW ACCUMULATOR

FIELD OF THE INVENTION

The invention relates to controlling fluid flow; and more specifically, to controlling fluid flow by pressurizing a fluid filled container.

Background of the Invention

It is known to control fluid flow to a patient by hanging a fluid container above the patient, pumping fluid into the container, and controlling fluid flow down to the patient by adjusting the height of the container or by placing a constant weight on top of a fluid container which is resting on a surface, thereby producing a pressure in the container, the pressure causing fluid flow to be adjusted.

It is also known to use pneumatically actuated systems to control pressure within a flexible fluid filled container.

Summary of the Invention

It has been discovered that variably pressurizing a flexible, fluid filled container by positioning the container between preloaded constraining surfaces produces an adjustable, predetermined flow through the container.

PREFERRED EMBODIMENT

The attached drawings illustrate the preferred embodiment, the structure and operation of which is then described.

Drawings

Structure

Figure 1:
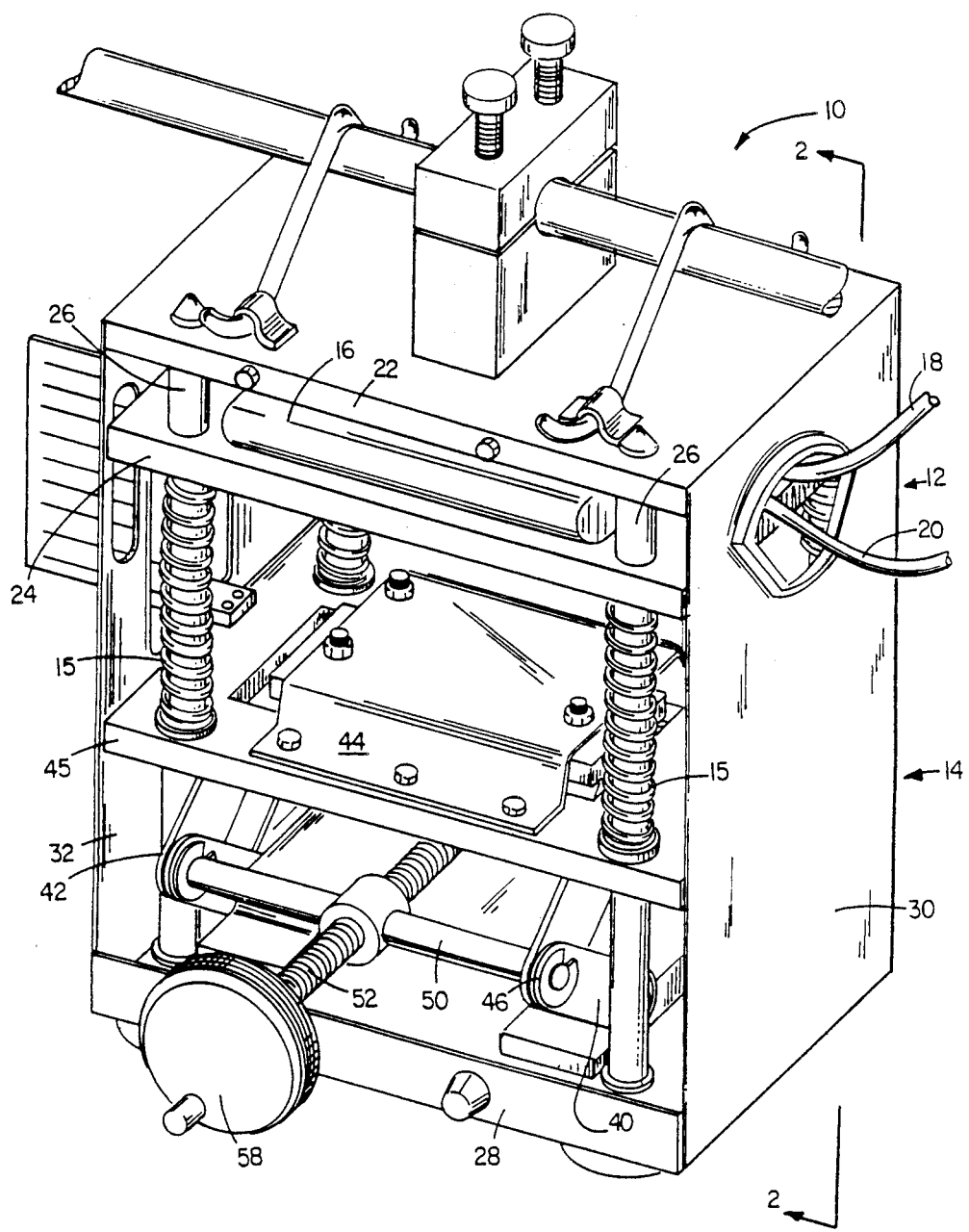
FIG. 1 is a perspective view of a fluid flow control apparatus according to the present invention.
Figure 2:
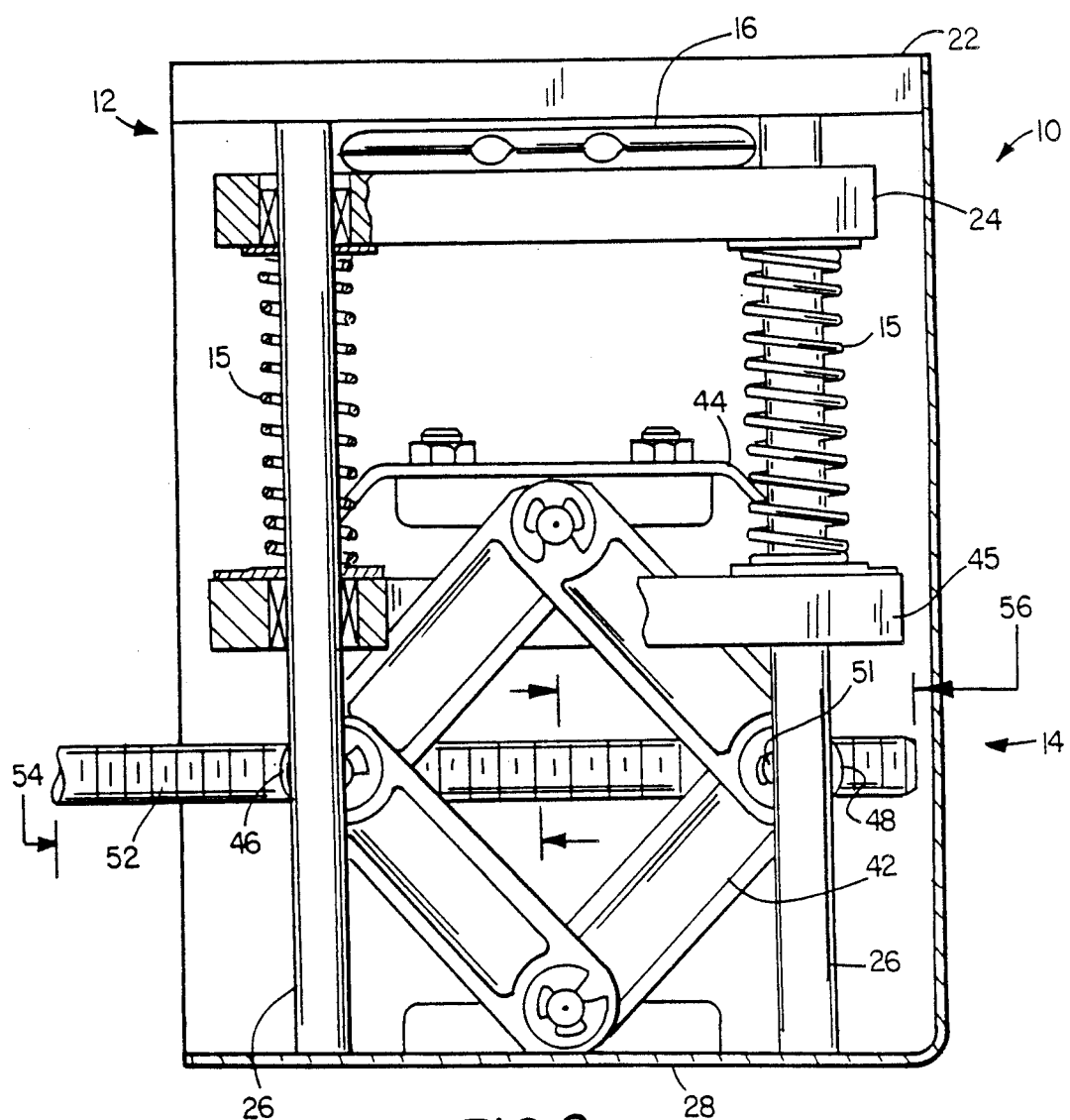
FIG. 2 is a cross-sectional view along the line 2—2 of the FIG. 1 fluid flow control apparatus.

Referring to FIGS. 1 and 2, fluid flow control apparatus 10 includes fluid flow portion 12 and actuating portion 14. Spring members 15 resiliently connect actuating portion 14 and fluid flow portion 12.

Fluid flow portion 12 includes flexible fluid container 16 having inlet 18 and outlet 20. Container 16 is constrained between fixed top plate 22 and movable bottom plate 24. Movable bottom plate 24 is guided by four guide bars 26, which are vertically oriented between fixed top plate 22 and fixed bottom plate 28. Also connected between top plate 22 and bottom plate 28 are walls 30, 32. Walls 30, 32 define apertures through which inlet 18 and outlet 20 pass.

Actuating portion 14 includes two scissors jacks 40, 42 which are secured between fixed bottom plate 28 and movable top plate 44. Movable top plate 44 is attached to movable frame 45 which is guided by guide bars 26. Scissors jacks 40, 42 are connected at their horizontal pivot points 46, 48 by horizontal rods 50, 51. Horizontal rods 50, 51 are connected by leadscrew 52 having left hand threaded portion 54 mating with threads of rod 50 and right hand threaded portion 56 mating with threads of rod 51. Handle 58 is attached to one end of leadscrew 52.

Operation

Referring to FIGS. 1 and 2, the flow rate of fluid flowing through fluid flow portion 12 is controlled by pressurizing flexible container 16 of fluid flow portion 12 with actuating portion 14.

More specifically, scissors jacks 40, 42 are actuated by rotating handle 58. Rotating handle 58 causes leadscrew 52 to rotate, thus causing rods 50, 51 to move due to left hand threaded portion 54 and right hand threaded portion 56 mating with rods 50, 51. Actuating scissors jacks 40, 42 moves movable frame 45 up or down along rods 26. This movement is translated via spring members 15 to move movable bottom plate 24. The increasing mechanical advantage of scissors jacks 40, 42 acts against the increasing pressurizing spring force of spring members 15 to provide a smooth force to movable bottom plate 24. The force of movable bottom plate 24, in combination with fixed top plate 22, provides a smooth pressure to flexible container 16. Flow through flexible container 16 is determined by applying Bernoulli's equation to the system (e.g., a dialysis or apheresis system) in which fluid flow control apparatus 10 is used. i.e., $$v = \left(\frac{2gp}{w}\right)^{\frac{1}{2}}$$

where,
v = velocity of fluid flow through flexible container 16;
g = acceleration of gravity;
p = pressure within flexible container 16;
and
w = specific weight of the fluid.

More specifically, for the apheresis application, $$v = \left(2g\left(\frac{p - \Delta p}{w} + \Delta Z\right)\right)^{\frac{1}{2}}$$

where,
$\Delta p$ = pressure drop from flexible container to outlet;
and
$\Delta$ = head from container to outlet.

What is claimed is:

1. A fluid flow control apparatus comprising
a flexible fluid container having an opening for the flow of fluid therethrough,
a fluid flow portion configured to receive and apply a flexible wall deflecting force to said flexible fluid container,
a spring member positioned to apply a spring force to said fluid flow portion, and
an adjustable actuating portion, said adjustable actuating portion acting upon said spring member to provide an adjustable spring force to said fluid flow portion, said fluid flow portion providing said flexible wall deflecting force to said flexible fluid container and thereby controlling fluid pressure therein, said fluid pressure controlling flow from said flexible fluid container.

2. The apparatus of claim 1 wherein said actuating portion includes a scissors jack.

3. The apparatus of claim 2 wherein said scissors jack is actuated by a lead screw.

4. The apparatus of claim 3 wherein said lead screw has first and second threaded portions, said first threaded portion having threads oriented in a first direction, said second threaded portion having threads oriented in a second direction.

5. The apparatus of claim 4 wherein said first direction is a right hand orientation and said second direction is a left hand orientation.

6. The apparatus of claim 1 wherein said flexible fluid container is received between a fixed plate and a movable plate of said fluid flow portion, said spring member applying said spring force to said movable plate.

* * * * *